United States Patent
Carlson (10) Patent No.: US 9,351,956 B1
(45) Date of Patent: May 31, 2016

(54) PHARMACEUTICAL COMPOSITION COMPRISING AN ENANTIOMER OF LIPOAMIDE AND DERIVATIVES THEREOF AND METHOD OF USE

(71) Applicant: David Carlson, Fairfax, CA (US)

(72) Inventor: David Carlson, Fairfax, CA (US)

(73) Assignee: GeroNova Research Inc., Fairfay, CA (US)

( * ) Notice: Subject to any disclaimer, the term of this patent is extended or adjusted under 35 U.S.C. 154(b) by 358 days.

(21) Appl. No.: 13/922,064

(22) Filed: Jun. 19, 2013

Related U.S. Application Data (60) Provisional application No. 61/662,215, filed on Jun. 20, 2012.

(51) Int. Cl.
*A61K 31/385* (2006.01)

(52) U.S. Cl.
CPC .................................. *A61K 31/385* (2013.01)

(58) Field of Classification Search
CPC ................................................... A61K 31/385
See application file for complete search history.

(56) References Cited

PUBLICATIONS

Arivazhagan et al (Experimental Gerontology 37 (2001) 81-87).*

Guo et al., "Inhibitory effect of alpha-lipoic acid and its positively charged amide analogue on nitric oxide production in RAW 264.7 macrophages", Biochem. Pharmacol. 61(5) pp. 547-554 (2001).
Kim et al., Polymeric worm micelles as nano-carriers for drug delivery, Nanotechnology 16, pp. S484-S491 (2005).
Lorenceau et al., "Generation of polymerosomes from double-emulsions", Langmuir 21, pp. 9183-9186 (2005).
Pautot et al., "Production of Unilamellar vesicles using an inverted emulsion", Langmuir 19, pp. 2870-2879 (2003).
Persson et al., "Alpha-lipoic acid and alpha-lipoamide prevent oxidant-induced lysosomal rupture and apoptosis", Redox Rep. pp. 327-334 (2001).
Sen et al., "A positively charged alpha-lipoic acid analogue with increased cellular uptake and more potent immunomodulatory activity", Biochem. Biophys. Res. Commun. 247(2), pp. 223-228 (1998).
Shen et al., "Therapeutic potential of lipoamide and enhanced mitochondrial biogenesis for treatment of insulin resistance", Chapter 5 in Mitochondrial Signaling in Health and Disease pp. 93-111 (2012).
Tirosh et al., "Neuroprotective effects of alpha-lipoic acid and its positively charged amide analogue", Free Radic. Biol. Med. 26, pp. 1418-1426 (1999).
Tirosh et al., "Redox regulation of mitochondrial permeability transition: Effects of uncoupler, lipoic acid and its positively charged analog LA-plus and selenium", BioFactors. vol. 17, issue 1-4, pp. 297-306 (2003).

* cited by examiner

*Primary Examiner* — Benjamin Packard (57) ABSTRACT

This invention is directed to pharmaceutical compositions comprising substantially enantiomerically pure lipoamide and derivatives thereof and methods of use of such compositions to modulate signaling pathways for the treatment of diseases and disorders.

4 Claims, 11 Drawing Sheets

Figure 1

| Signaling pathways | Regulatory element | Transcription Factor |
| --- | --- | --- |
| 1. Amino Acid Deprivation | AARE | ATF4/ATF3/ATF2 |
| 2. Androgen | AR | Androgen Receptor |
| 3. Antioxidant Response | ARE | Nrf2 & Nrf1 |
| 4. ATF6 | ATF6 | ATF6 |
| 5. C/EBP | C/EBP | C/EBP |
| 6. cAMP/PKA | CRE | CREB |
| 7. Cell Cycle | E2F/DP1 | E2F/DP1 |
| 8. DNA Damage | P53 | p53 |
| 9. EGR1 | EGR1 | EGR1 |
| 10. ER Stress | CBF/NF-Y/YY1 | ERSE |
| 11. Estrogen | ER | Estrogen Receptor |
| 12. GATA | GATA | GATA Receptor |
| 13. Glucocorticoid | GR | Glucocorticoid Receptor |
| 14. Heat Shock | HSF | HSF |
| 15. Heavy Metal Stress | MTF1 | MTF1 |
| 16. Hedgehog | GLI | GLI |
| 17. HNF4 | HNF4 | HNF4 |
| 18. Hypoxia | HIF | HIF1a |
| 19. Interferon Regulatory Factor | IRF1 | IRF1 |
| 20. Interferon Type 1 | ISRE | STAT1/STAT2 |
| 21. Interferon Gamma | GAS | STAT1 |
| 22. KLF4 | KLF4 | KLF4 |
| 23. Liver X Receptor | LXR | LXR |
| 24. MAPK/ERK | SRE | ELK1/SRF |
| 25. MAPK/JNK | AP1 | AP1 |
| 26. MEF2 | MEF2 | MEF2 |
| 27. Myc | Myc | Myc/Max |
| 28. Nanog | Nanog | Nanog |
| 29. Notch | RBP-Jk | RBP-Jk |
| 30. NFkB | NFkB | NFkB |
| 31. Oct4 | Oct4 | Oct4 |
| 32. Pax6 | Pax6 | Pax6 |
| 33. PI3K/AKT | FoxO | FoxO |
| 34. PKC/Ca²⁺ | NFAT | NFAT |
| 35. PPAR | PPAR | PPAR |
| 36. Progesterone | Progesterone | Progesterone Receptor |
| 37. Retinoic Acid | RARE | Retinoic Acid Receptor |
| 38. Retinoid X | RXR | RXR |
| 39. Sox2 | Sox2 | Sox2 |
| 40. SP1 | SP1 | SP1 |
| 41. STAT3 | STAT3 | STAT3 |
| 42. TGFβ | SMAD | SMAD2/3/4 |
| 43. Vitamin D | VDRE | VitaminD Receptor |
| 44. Wnt | TCF/LEF | TCF/LEF |
| 45. Xenobiotic | XRE | AhR |

PHARMACEUTICAL COMPOSITION COMPRISING AN ENANTIOMER OF LIPOAMIDE AND DERIVATIVES THEREOF AND METHOD OF USE

RELATED APPLICATIONS

This application claims the benefit of U.S. Provisional Patent Application Ser. No. 61/662,215 filed on 20 Jun. 2012.

FIELD

This invention relates to substantially pure single enantiomer lipoamide and derivatives thereof and use of the compounds as pharmaceutical agents and as dietary supplements.

BACKGROUND

Lipoic acid (LA) is a sulfur containing medium chain fatty acid (C8) with a single chiral center (C6) and thus exists as two enantiomers, the naturally occurring R-(+)-lipoic acid (RLA) and S-(−)-Lipoic acid (SLA) but is generally administered as a racemic (50:50) mixture (RS-LA) for pharmaceutical and nutraceutical applications. It is an established principle of pharmacology that a single enantiomer frequently displays different pharmacodynamic (PD) profiles relative to the racemate or to its antipode. Few studies have attempted to characterize the enantioselective, non-enantioselective, quantitative and qualitative similarities and differences in the mechanisms of action between the three forms of LA, which, until clearly defined, should be considered pharmacologically distinct.

This invention, then is directed to the characterization and comparison of enantiomeric and racemic RLA and SLA as well as enantiomeric and racemic lipoamide and derivatives thereof and to pharmaceutical compositions comprising the latter, which have demonstrated surprising superior pharmacological properties and are the focus of this invention.

DETAILED DESCRIPTION

Brief Description of the Figures

The figures provided herein are intended solely as an aid in understanding the invention and are not, and should not, be construed as limiting the scope of this invention in any manner whatsoever.

The abscissa of each of the graphs shown in FIGS. 3-8 is the fold-changes compared to control values.

In FIG. 9-11, al expression pathways were included in the analysis.

DISCUSSION

Figure 1:
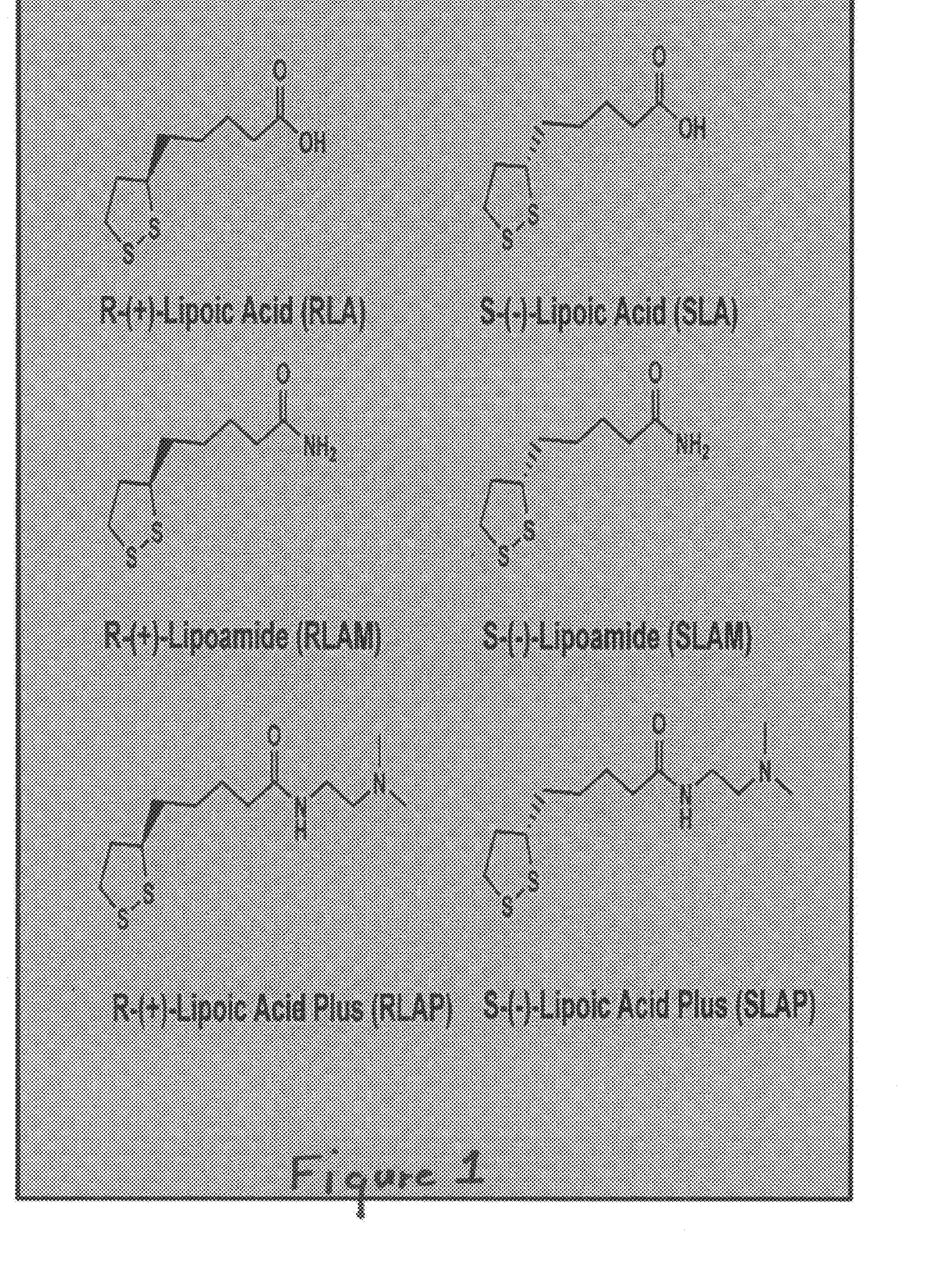
FIG. 1 shows the chemical structure of R-(+)-lipoic acid (RLA), R-(+)-lipoamide (RLAM), a positively charged derivative of RLAM, N-2-dimethylammoniumethyl)-(R)-(+)-lipoamide (RLAP), S-(−)-lipoic acid (SLA), S-(−)-lipoamide (SLAM) and a positively charged derivative of SLAM, N-2-dimethylammoniumethyl)-(S)-(−)-lipoamide (SLAP).
Figure 2:
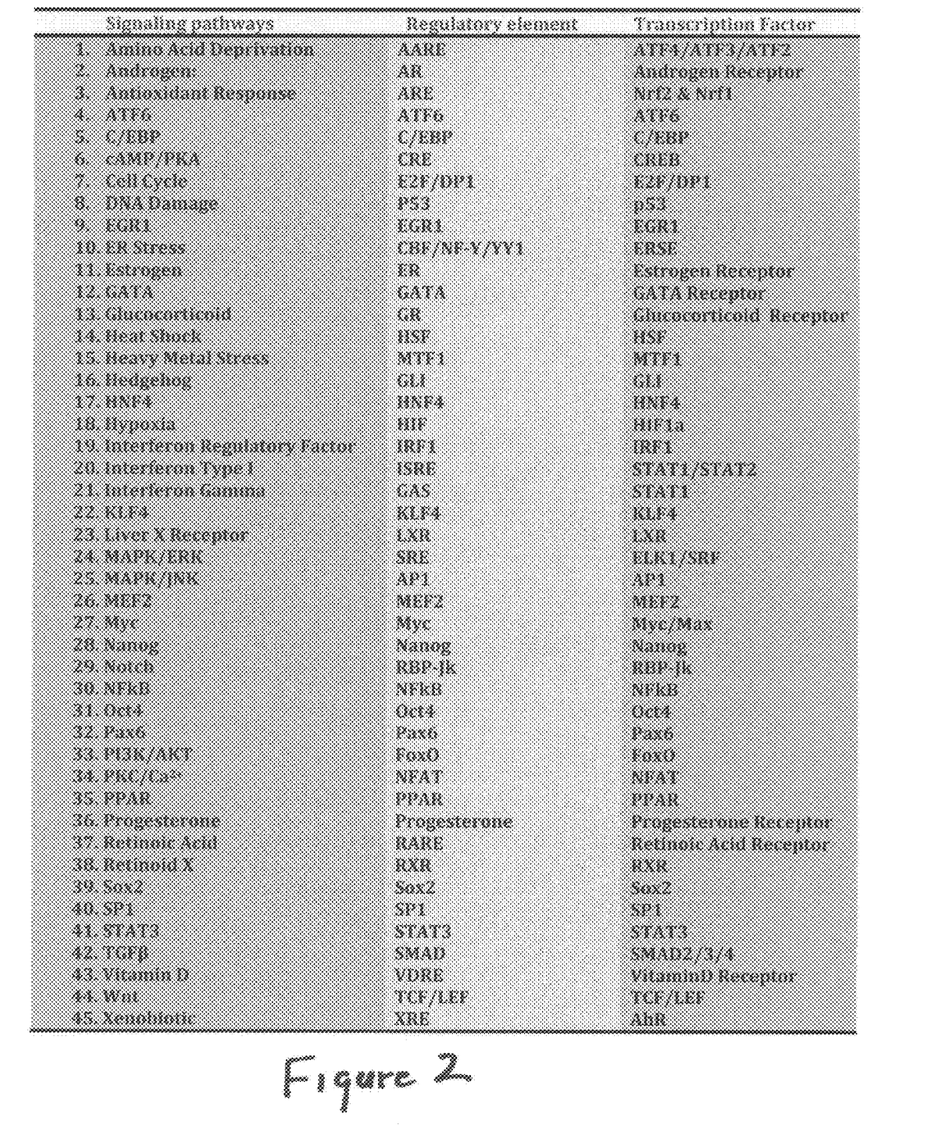
FIG. 2 shows a non-limiting group of signaling pathways, regulatory elements and transcription factors that may be affect by a pharmaceutical composition of this invention.
Figure 3:
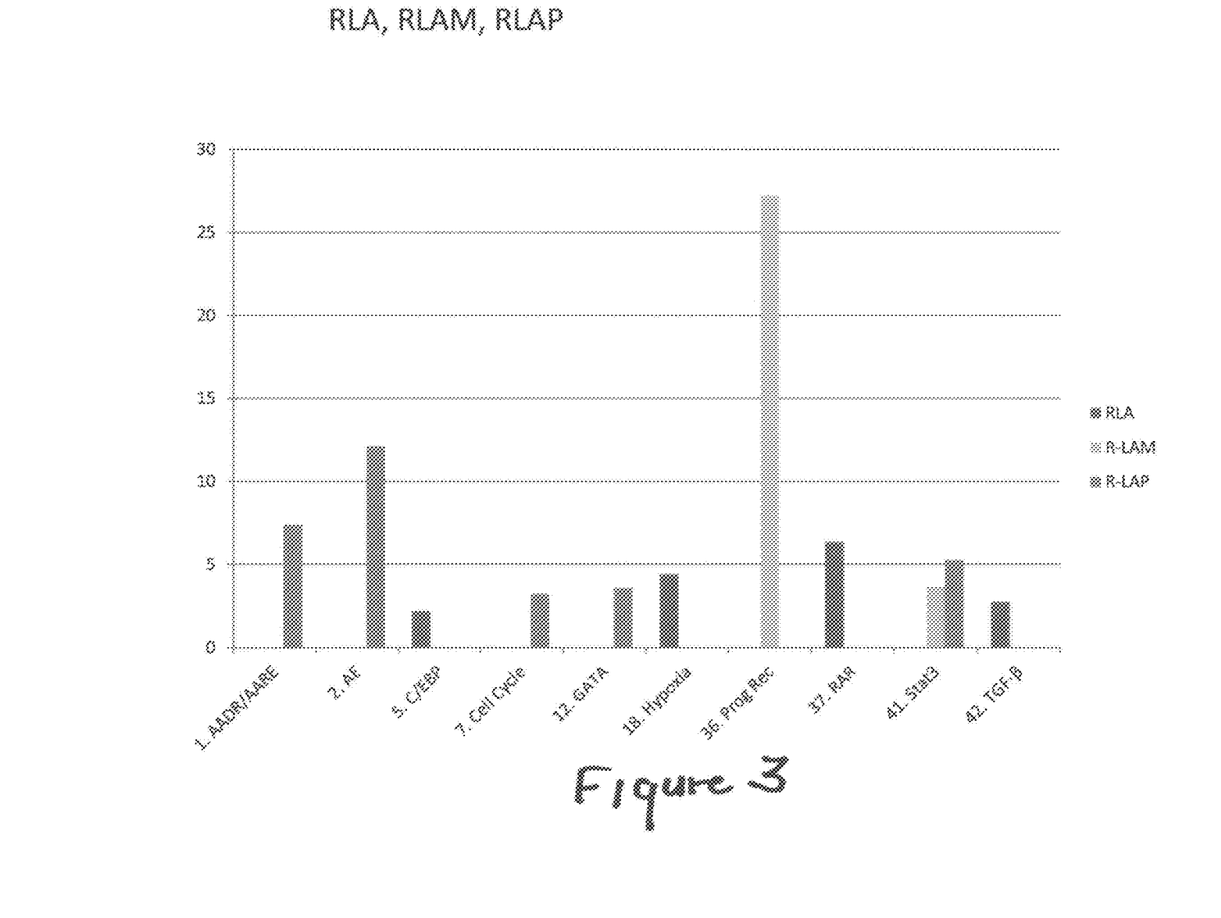
FIG. 3 shows a comparison of the degree of induction of various signaling pathways by RLA, RLAM and RLAP.
Figure 4:
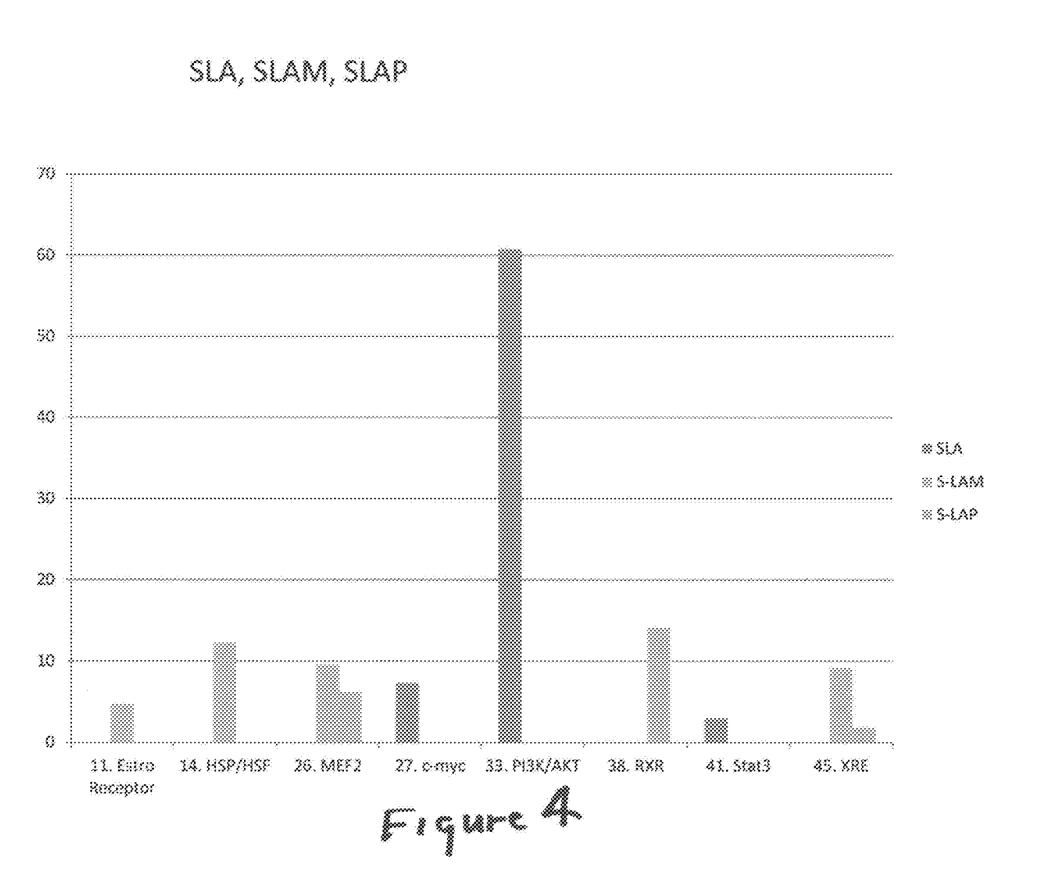
FIG. 4 shows a comparison of the degree of induction of various signaling pathways by SLA, SLAM and SLAP.
Figure 5:
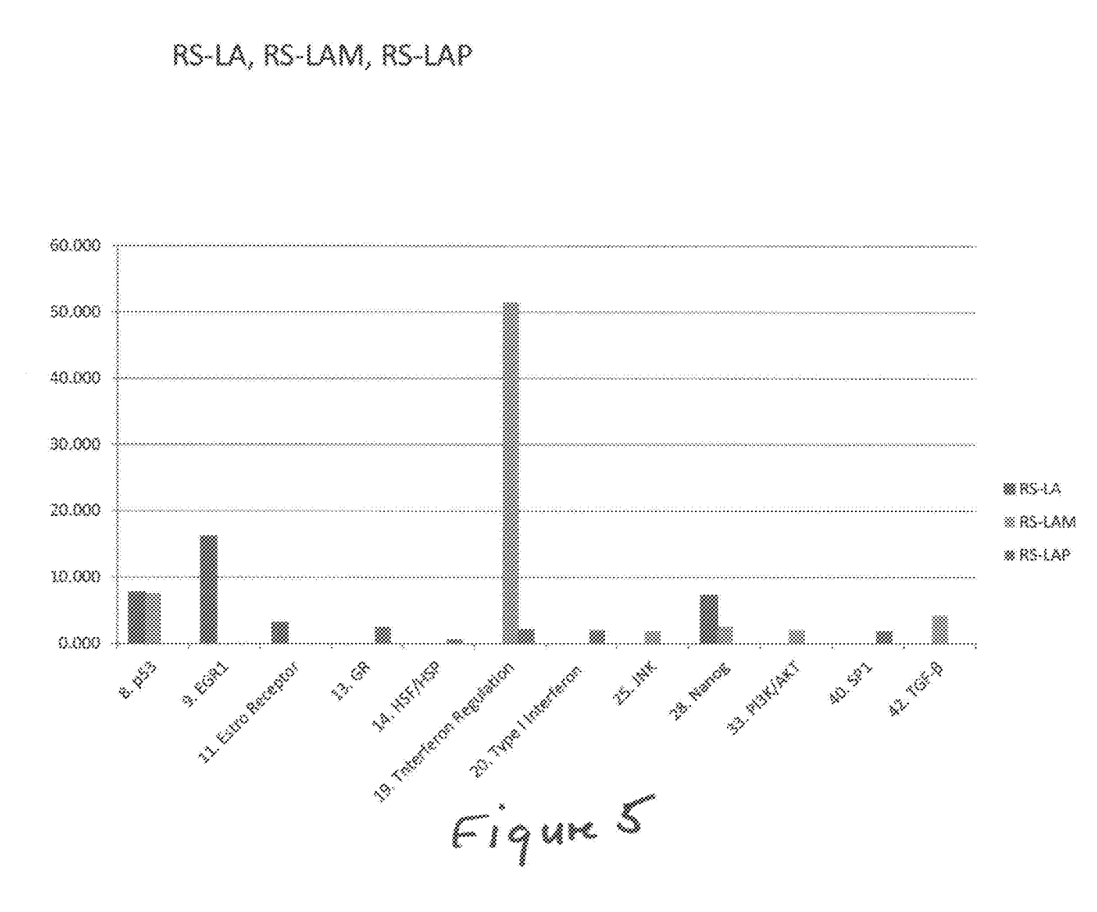
FIG. 5 shows a comparison of the degree of induction of various signaling pathways by racemic mixtures of RLA and SLA (RS-LA), racemic mixture of RLAM and SLAM (RS-LAM) and racemic mixture of RLAP and SLAP (RS-LAP).
Figure 6:
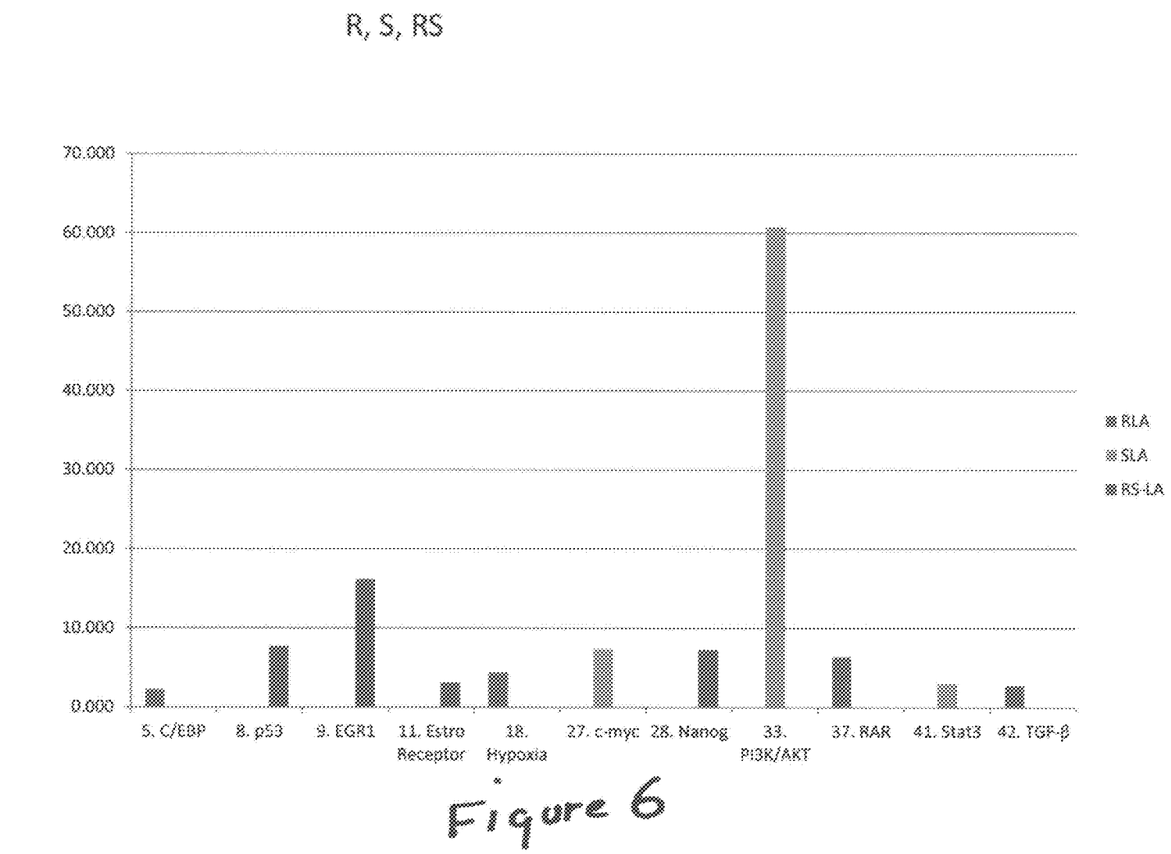
FIG. 6 shows a comparison of the fold induction of various signaling pathways by RLA, SLA and RS-LA.
Figure 7:
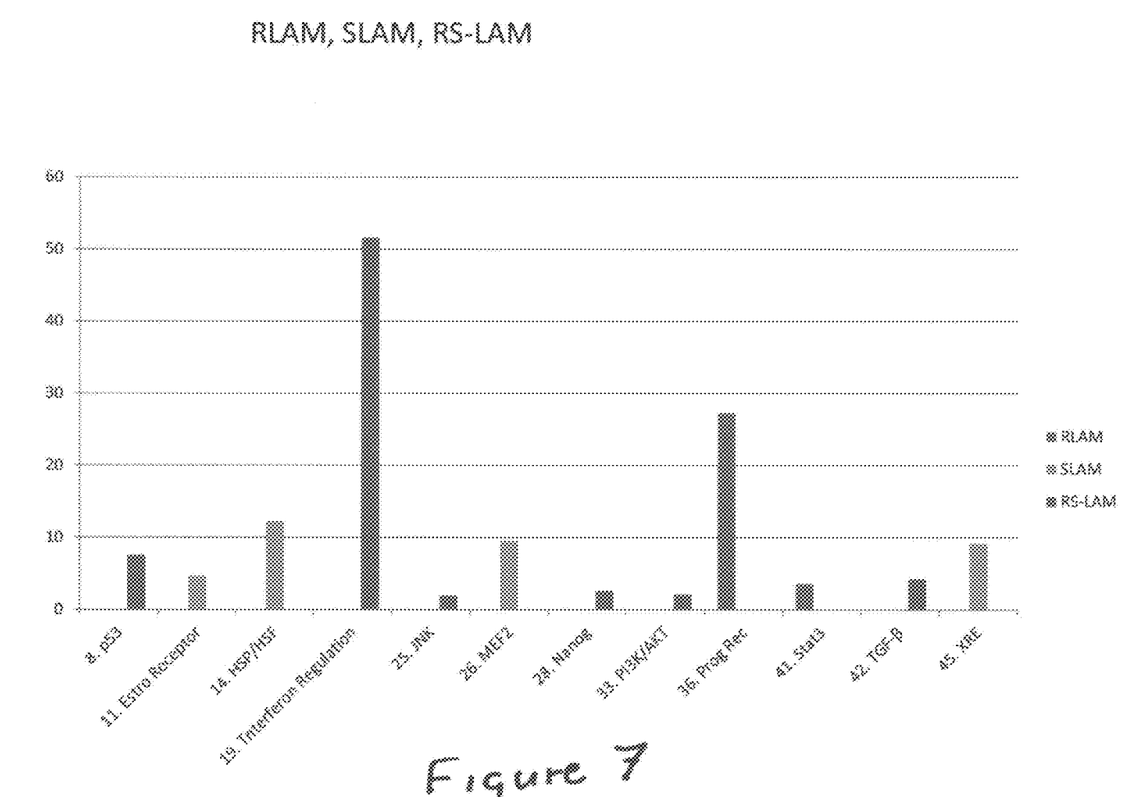
FIG. 7 shows a comparison of the fold induction of various signaling pathways by RLAM, SLAM and RS-LAM.
Figure 8:
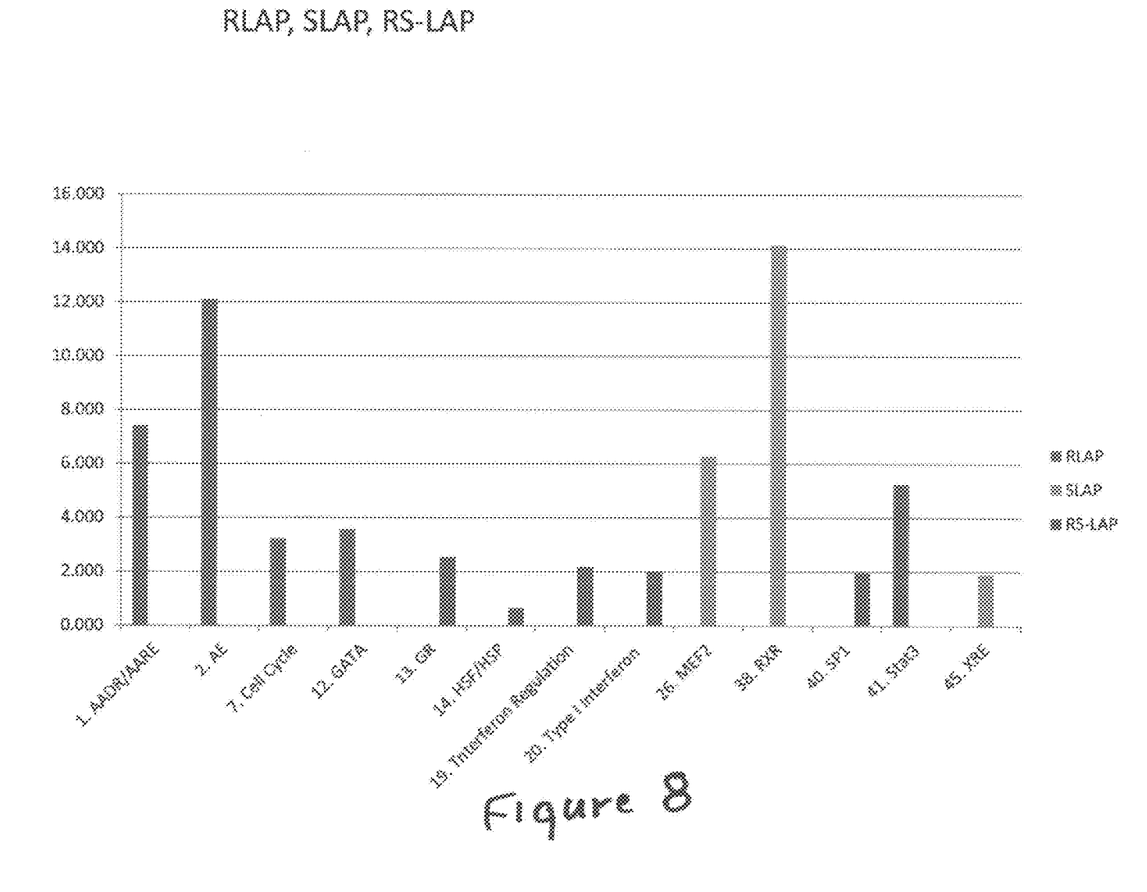
FIG. 8 shows a comparison of the fold induction of various signaling pathways by RLAP, SLAP and RS-LAP.
Figure 9:
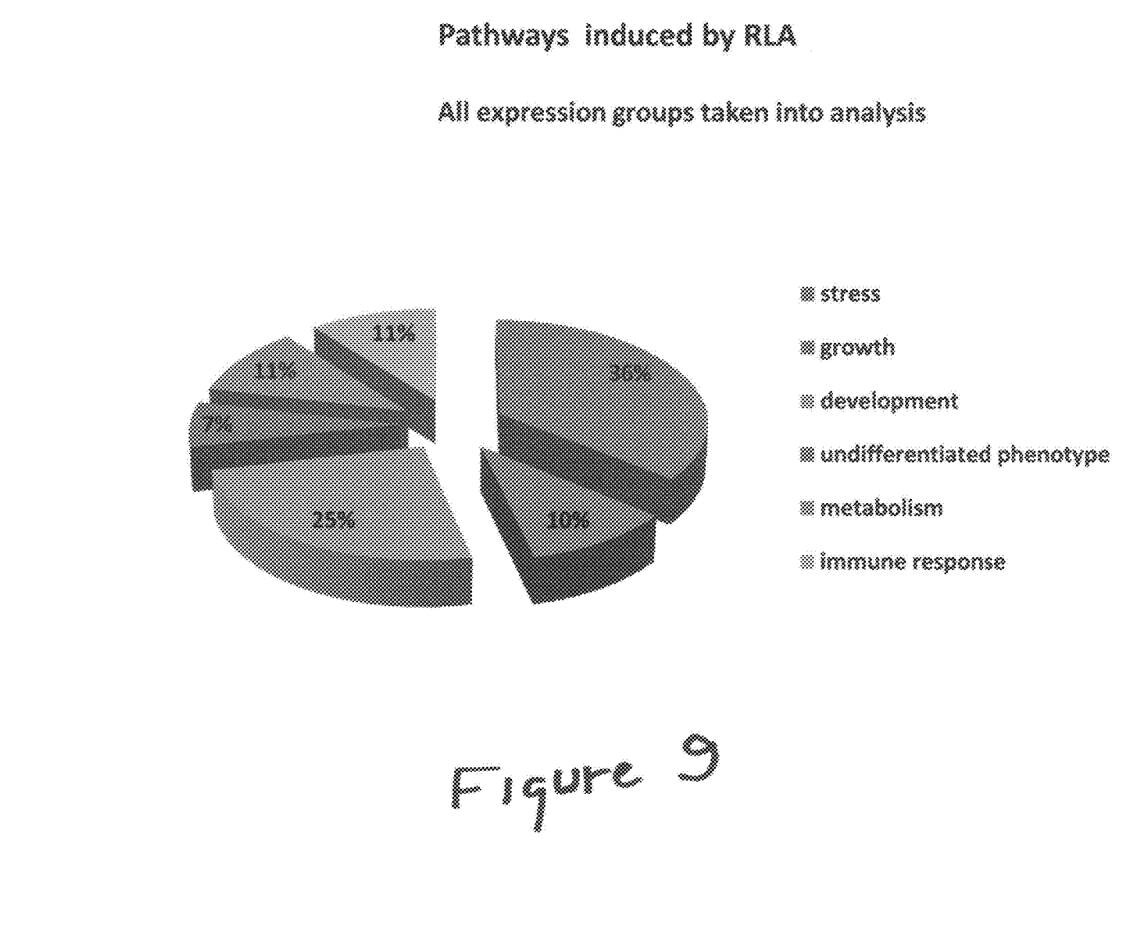
FIG. 9 shows a pie chart of signaling pathways that are induced by RLA.
Figure 10:
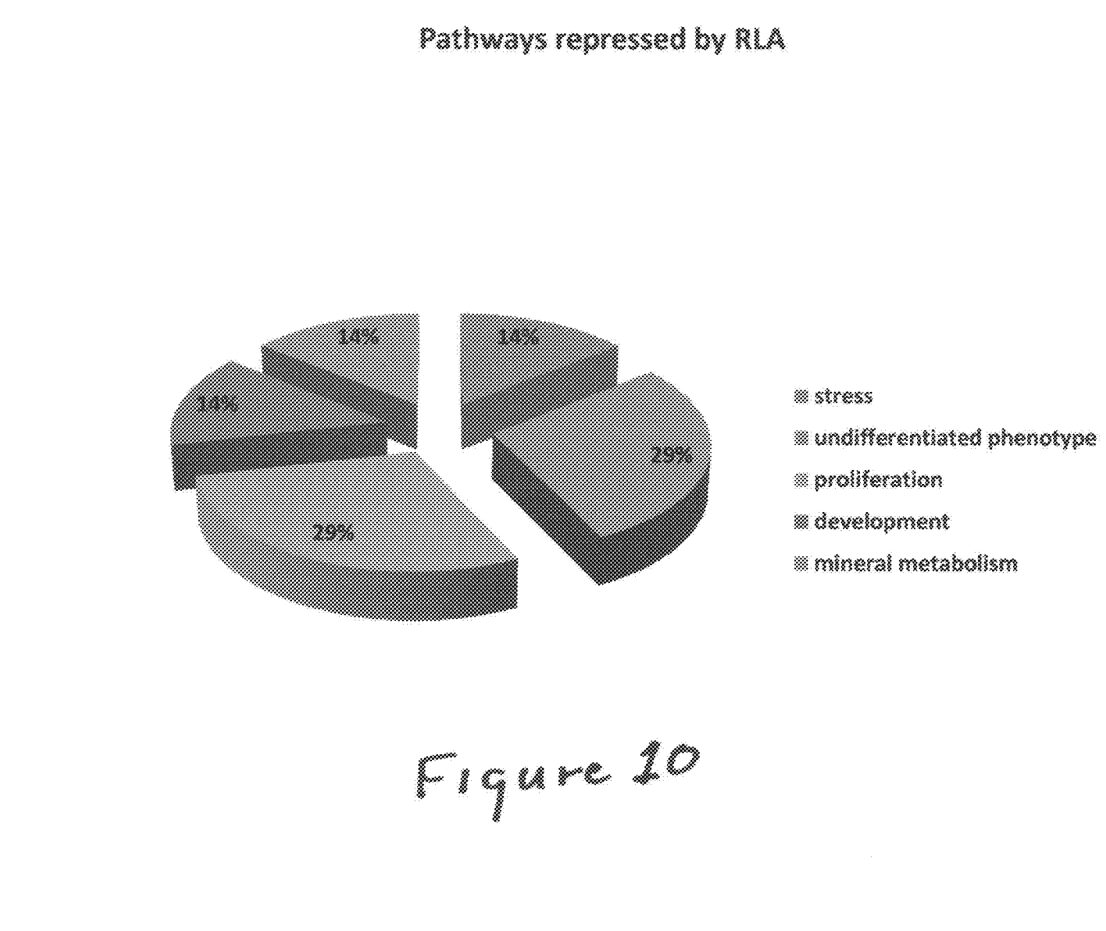
FIG. 10 shows a pie chart of signaling pathways that are repressed by RLA.
Figure 11:
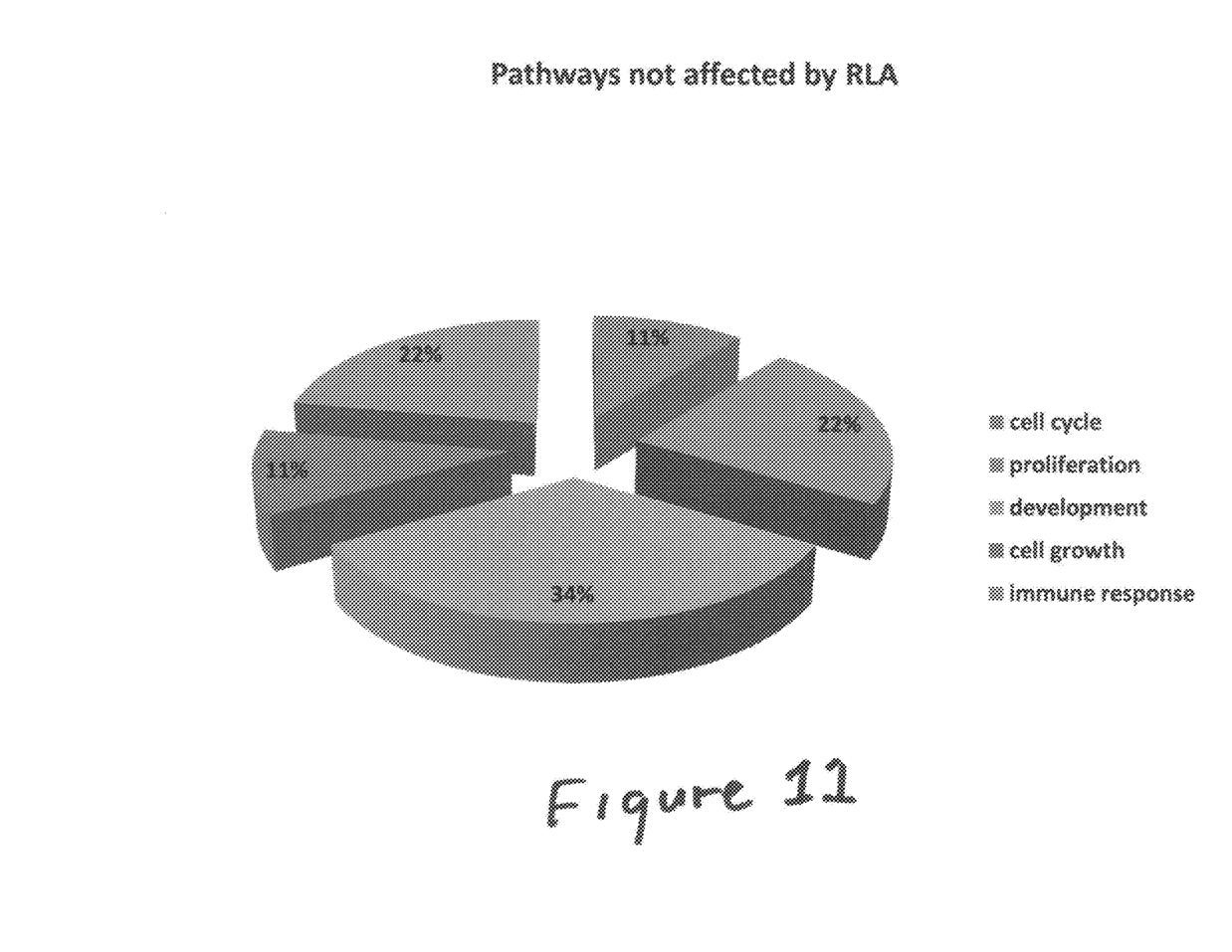
FIG. 11 shows pathways not affected by RLA.

It is understood that use of the singular throughout this application including the claims includes the plural and vice versa unless expressly stated otherwise. That is, "a" and "the" are to be construed as referring to one or more of whatever the word modifies. Non-limiting examples are: "a pharmaceutically acceptable carrier or excipient," which is understood to include one or more such carrier or excipient, and "a biochemical methyl donor," which is understood to include one or more such donors, unless it is expressly stated or is unambiguously obvious from the context that such is not intended.

As used herein, words of approximation such as, without limitation, "about," "substantially," "essentially" and "approximately" mean that the word or phrase modified by the term need not be exactly that which is written but may vary from that written description to some extent. The extent to which the description may vary will depend on how great a change can be instituted and still have one of ordinary skill in the art recognize the modified version as still having the properties, characteristics and capabilities of the modified word or phrase. In general, but subject to the preceding discussion, a numerical value herein that is modified by a word of approximation may vary from the stated value by ±15%.

As used herein, the use of "preferred," "preferably," or "more preferred," and the like refer to preferences as they existed at the time of filing of this patent application.

In vitro assays have shown that substitution of the free carboxyl group of LA with ammonia or dimethylaminoethylamine yielding neutral (LAMs) and positively charged amides (LAPs), respectively has led to derivatives with either more active transport, greater intracellular $T_{1/2}$, altered subcellular distribution, higher concentrations and accumulations of the reduced forms as well as higher potency than LA in some cell types and models (references 1-6). To date, there are no published studies attempting to correlate the pharmacokinetics (PK) and PD of LA or to interpret the PD in terms of the common and differential effects of enantioselectivity and amide substitution on redox sensitive signaling pathways.

Thus, in general, this invention relates to a pharmaceutical composition comprising R-(+)-lipoamide or an N-substituted derivative thereof, or S-(−)-lipoamide or an N-substituted derivative, wherein the selected enantiomer is substantially free of the other enantiomer; and a pharmaceutically acceptable carrier. The pharmaceutical composition is presently preferred to comprise an N-substituted derivative of R(+)-lipoamide or S-(−)-lipoamide which has the formula N—($R_1R_2N(CH_2)_x$)—R(+)-lipoamide or N—($R_1R_2N(CH_2)_x$)—S-(−)-lipoamide, wherein x is 2-20 and $R_1$ and $R_2$ are independently hydrogen or (C1-C20)alkyl. The x is presently preferred to be 2 and $R_1$ and $R_2$ are both methyl. "C1-C20" means that the alkyl group may comprise from 1 to 20 carbon atoms.

In an embodiment of this invention the N-substituted derivative of R-(+)-lipoamide or S-(−)-lipoamide, comprises a salt having the formula $(R_1R_2NH^+(CH_2)_x)$—R(+)-lipoamide $X^-$ or N—$(R_1R_2NH^+(CH_2)_x)$—S-(−)-lipoamide $X^-$, wherein X is a pharmaceutically acceptable counterion.

The pharmaceutical composition of this invention may further comprise a biochemical methyl donor. A biochemical methyl donor refers to a compound that, in physiological environs, is capable of methylating biochemical substances such as, without limitation, nucleic acids, proteins, enzymes and cell components, thereby altering the activity of the methylated species. Biochemical methyl donor include, without limitation, choline, betaine, carnitine, acetylcarnitine, folic acid, vitamin B-12 and methionine.

The pharmaceutical composition of this invention may also comprise hydroxycitric acid, preferably at present (2S,3R)-hydroxycitric acid, or a salt thereof.

The pharmaceutical composition of this invention may constitute a pharmaceutical drug, the administration of which is under the control of a licensed practitioner or it may constitute a dietary supplement which is available over the counter in which case administration of the composition is in the hands of the user.

A pharmaceutical composition of this invention may have the enantiomeric compound hereof in an pharmaceutically acceptable carrier which comprises a nanoparticle, a microparticle, a micelle, a liposome or a polymersome. In an embodiment of this invention, the pharmaceutically acceptable carrier may comprise a targeting moiety that targets the carrier to a specific location in a subject's body. The targeted location may be, without limitation, the heart, the cardiovascular system, the peripheral vasculature, the lungs, the kidneys, the pancreas, the small intestine, the large intestine, the thyroid, the liver, the retina and the aural system or a solid tumor located anywhere in a subject's body.

An embodiment of this invention comprises a method of treating a disease or disorder, sometimes referred to herein collectively as a "condition," in an subject comprising administrating to the subject in need thereof of a therapeutic amount of a pharmaceutical composition of this invention wherein the disease or disorder is selected from the group consisting of diabetes, diabetic neuropathy, glaucoma, cancer, kidney disease, age-related memory loss, Alzheimer's disease, atherosclerosis, bone loss, vascular disease, mitochondrial myopathy, multiple sclerosis muscular dystrophy, cerebrovascular disease, cognitive impairment, Down's syndrome, endothelial dysfunction, Hepatitis C, inflammation, high blood pressure, high cholesterol, neurodegenerative disease, obesity, Parkinson's disease, retinal leukostasis, retinal ischemia, retinal reperfusion, retinopathy, sepsis, sickle cell anemia, Wilson's disease, age-related loss of liver detoxification, age-related loss of liver regeneration, hepatic cancer, autoimmune disease, degenerative brain disorder, cerebral ischemia, AIDS or a hepatic disorder. In particular at present, the condition to be treated using a pharmaceutical composition of this invention is preferably age-related loss of liver detoxification, age-related loss of liver regeneration and hepatic cancer.

Generally, the method of this invention relates to conditions that involve certain signaling pathways, the modulation of which by a pharmaceutical composition of this invention can beneficially affect the well-being of a subject. Signaling pathways that may be modulated by a pharmaceutical composition of this invention include, without limitation, an amino acid deprivation, androgen, antioxidant response, ATF6, C/EBP, cAMP, PKA, cell cycle, DNA Damage, EGR1, ER stress, estrogen, GATA, glucocorticoid, heat shock, heavy metal stress, hedgehog, HNF4, hypoxia, interferon regulatory factor, interferon type I, interferon gamma, KLF4, liver receptor X, MAPK/ERK, MAPK/JNK, MEF2, Myc, Nanog, Notch, NFkB, Oct4, Pax6, PI3K/AKT, PKC/$Ca^{2+}$, PPAR, progesterone, retinoic acid, retinoid X, SOX2, SP1, STATA3, TGFβ, vitamin D, Wnt, or xenobiotic pathway.

As used herein, the term "pharmaceutical composition" refers to a mixture of a compound of this invention with other chemical components, such as diluents, carriers, excipients or any combination of these. The pharmaceutical composition facilitates administration of the compound to a subject.

As used herein, a "subject," refers to any organism that may benefit from treatment with a pharmaceutical composition of this invention. A presently preferred subject is a human being. A subject herein may also be referred to as a "patient;" the terms are interchangeable.

As used herein, the term "carrier" refers to a chemical or physical entity that facilitates the incorporation of a compound of this invention into cells or tissues. For example dimethyl sulfoxide (DMSO) is a commonly utilized chemical carrier as it facilitates the uptake of many organic compounds into the cells or tissues of an organism. Or the carrier may comprise a physical entity to which a compound of this invention or a pharmacological composition thereof adheres or within which the compound or composition is encapsulated. Examples of the latter are nano- and micro-particles, micelles, liposomes and polymersomes.

As used herein, the term "diluent" refers to chemical entities that are capable of dissolving compound of this invention as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound.

As used herein, the term "excipient" refers to supplemental compounds other than carriers and diluents such as, without limitation, sweeteners, surface active agents, fragrances, dyes, and flavoring substances.

As used herein, the term "pharmaceutically acceptable" refers to any component of a pharmaceutical composition of this invention that does not abrogate the biological activity and properties of the compound nor does it deleteriously affect any body part or function of a patient.

As used herein, the term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound of this invention with inorganic acids such as, without limitation, hydrochloric acid or hydrobromic acid, sulfuric acid, nitric acid or phosphoric acid. Pharmaceutical salts can also be obtained by reacting a compound of this invention with an organic acid such as, without limitation acetic, succinic, lactic, malic, tartaric, citric, ascorbic, nicotinic, methanesulfonic, ethanesulfonic, p-toluensulfonic, salicylic or naphthalenesulfonic acid.

The compounds of this invention can be used alone as essentially the only active component of a pharmaceutical composition hereof, or they may be used in combination with one or more other pharmaceutical agents that are known or suspected to be active as a therapeutic agent for the intended therapeutic use to which the pharmaceutical composition of this invention is being put.

As used herein, the terms "purified," "substantially purified," and "isolated" as used herein refer to the compounds of the invention being substantially free of other compounds including, in particular, the corresponding enantiomer of the indicated compound. By "substantially enantiomerically pure" is meant that the desired enantiomer is at least 90% enantiomerically pure, preferably at present least 95% enantiomerically pure and even more preferably at present at least 99% enantiomerically pure.

As used herein, "modulate" refers to the ability of a compound of this invention to alter the function of a given signaling pathway. A modulator may activate or enhance the activity of a signaling pathway, or it may inhibit or deactivate a signaling pathway, whichever will achieve the desired therapeutic response.

As used herein, "therapeutic agent" refers to any substance that, when administered in a therapeutically effective amount to a patient suffering from a condition, has a therapeutic beneficial effect on the health and well-being of the patient. A therapeutic beneficial effect on the health and well-being of a patient includes, but it not limited to: (1) curing the condition; (2) slowing the progress of the condition; (3) causing the condition to retrogress; or, (4) alleviating one or more symptoms of the condition. As used herein, a therapeutic agent also includes any substance that when administered to a patient, known or suspected of being particularly susceptible to a condition, in a prophylactically effective amount, has a prophylactic beneficial effect on the health and well-being of the patient. A prophylactic beneficial effect on the health and well-being of a patient includes, but is not limited to: (1) preventing or delaying on-set of the condition in the first place; (2) maintaining a condition at a retrogressed level once such level has been achieved by a therapeutically effective amount of a substance, which may be the same as or different from the substance used in a prophylactically effective amount; or, (3) preventing or delaying recurrence of the condition after a course of treatment with a therapeutically effective amount of a substance, which may be the same as or different from the substance used in a prophylactically effective amount, has concluded.

As used herein, "treating" refers to the administration of a therapeutically effective amount of a therapeutic agent to a subject known or suspected to be suffering from a condition with regard to which a compound or pharmaceutical composition comprising such compound of this invention has been demonstrated, or is deemed likely, to be effective.

A "therapeutically effective amount" refers to that amount of a therapeutic agent that will have a beneficial effect, which may be curative or palliative, on the health and well-being of the patient known or suspected to be afflicted by a condition. A therapeutically effective amount may be administered as a single bolus, as intermittent bolus charges, as short, medium or long term sustained release formulations or as any combination of these. As used herein, short-term sustained release refers to the administration of a therapeutically effective amount of a pharmaceutical composition of this invention over a period from about several hours to about 3 days. Medium-term sustained release refers to administration of a therapeutically effective amount of a therapeutic agent over a period from about 3 day to about 14 days and long-term refers to the delivery of a therapeutically effective amount over any period in excess of about 14 days.

An embodiment of this invention relates to a pharmaceutical composition comprising physiologically acceptable surface active agents, carriers, diluents, excipients, smoothing agents, suspension agents, film-forming substances, and coating assistants, or a combination thereof; and a compound of this invention.

Pharmaceutically acceptable carriers or diluents for therapeutic use are well known in the pharmaceutical art, and are described, for example, in Remington's Pharmaceutical Sciences, 18th Ed., Mack Publishing Co., Easton, Pa. (1990). Preservatives, stabilizers, dyes, sweeteners, fragrances, flavoring agents, and the like may be provided in the pharmaceutical composition. For example, sodium benzoate or ascorbic acid may be added as a preservative. Alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

Suitable routes of administration of the pharmaceutical compositions of this invention include, without limitation, oral, rectal, transmucosal, topical, intestinal, parenteral, intramuscular, subcutaneous, intravenous, intrathecal, intraventricular, intraperitoneal, intranasal and intraocular. The compositions can also be administered in sustained or controlled release dosage forms for prolonged administration at a predetermined rate.

The pharmaceutical compositions of the present invention may be manufactured by any means known in the art including, without limitation, simple mixing, dissolving, granulating, dragee forming, emulsifying, encapsulating, entrapping or tableting processes.

Proper formulation is dependent upon the route of administration chosen. The correlation of formulation with route of administration is well-known to those skilled in the art. For example, Remington's Pharmaceutical Sciences contains substantial teachings relating to method of administration and preferred formulations.

For example, with regard to oral administration, a presently preferred route, the compounds of this invention can be formulated readily by combination with pharmaceutically acceptable carriers well known in the art that enable the compounds to be formulated as, without limitation, tablets, pills, dragees, capsules, liquids, gels, syrups, slurries and suspensions. Suitable excipients such as sugars (without limitation, lactose, sucrose, mannitol, sorbitol or any combination thereof); cellulosics such as, without limitation, maize starch, wheat starch, rice starch, potato starch, gelatin, gum tragacanth, methyl cellulose, hydroxypropylmethyl-cellulose, polyvinylpyrrolidone and combinations thereof may also be added. If desired, disintegrating agents may be added, such as, without limitation, cross-linked polyvinyl pyrrolidone, agar, alginic acid or sodium alginate. Dragee cores may be provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

For buccal administration, the compositions may be formulated as tablets or lozenges.

Pharmaceutical compositions for intraocular delivery include aqueous ophthalmic solutions of the active compounds in water-soluble form for administration as eye drops in gellan gum or hydrogels, or in ophthalmic ointments or ophthalmic suspensions or in lipid soluble formulations and ocular inserts.

Pharmaceutical compositions for intranasal delivery may also include drops and sprays often prepared to simulate nasal secretions to ensure maintenance of normal ciliary action.

Pharmaceutical compositions for intra-auricular delivery include suspensions and ointments for topical application in the ear using such common solvents as glycerin and water.

The pharmaceutical composition of this invention may include a compound of this invention per se or the compound may be formulated in a carrier such as, without limitation, a nanoparticle, a microparticle, a micelle, a worm micelle, a liposome or a polymersome.

As used herein, a "nanoparticle" refers to a solid having as its largest cross-sectional, i.e., through the solid as opposed to along its surface, dimension of no greater than 100 nanometers. The solid can have any desired shape although substantially spherical particles are well-known in the art, are readily prepared and are presently preferred. By "substantially spherical" is meant that the particles need not have a surface that mimics a table tennis ball, i.e., virtually perfectly spherical but rather may by odd-shaped but would be considered generally "round" by one of skill in the art.

A microparticle has the same characteristics as a nanoparticle except that its smallest cross-sectional dimension is greater than 100 nm. The maximum size of a microparticle will depend at least in part on the route of administration, e.g., without limitation, oral, subcutaneous implantation, interperitoneally, etc. and will be readily determinable by the skilled artisan A micelle refers to a spherical colloidal core-shell structure spontaneous formed by many amphiphilic molecules in an aqueous medium when the Critical Micelle Concentration (CMC) is exceeded. Amphiphilic molecules have two distinct components, differing in their affinity for a solute, most particularly water. The part of the molecule that has an affinity for water, a polar solute, is said to be hydrophilic. The part of the molecule that has an affinity for non-polar solutes such as hydrocarbons is said to be hydrophobic. When amphiphilic molecules are placed in water, the hydrophilic moiety seeks to interact with the water while the hydrophobic moiety seeks to avoid the water. To accomplish this, the hydrophilic moiety remains in the water while the hydrophobic moiety is held above the surface of the water in the air or in a non-polar, non-miscible liquid floating on the water. The presence of this layer of molecules at the water's surface disrupts the cohesive energy at the surface and lowers surface tension. Amphiphilic molecules that have this effect are known as "surfactants." Only so many surfactant molecules can align as just described at the water/air or water/hydrocarbon interface. When the interface becomes so crowded with surfactant molecules that no more can fit in, i.e., when the CMC is reached, any remaining surfactant molecules will form into spheres with the hydrophilic ends of the molecules facing out, that is, in contact with the water forming the micelle corona and with the hydrophobic "tails" facing toward the center of the of the sphere. Therapeutic agents suspended in the aqueous medium can be entrapped and solubilized in the hydrophobic center of micelles which can result in an increase in the bioavailability as well as improving the stability in biological surroundings, improving the pharmacokinetics and possibly decreasing the toxicity of the therapeutic agent. In addition because of their nanoscale size, generally from about 5 nm to about 50 nm, micelles have been shown to exhibit spontaneous accumulation in pathological areas with leaky vasculature and impaired lymphatic drainage, a phenomenon known as the Enhanced Permeability and Retention or EPR effect.

The problem with micelles formed from relatively low molecular weight surfactants is that their CMC is usually quite high so that the formed micelles dissociate rather rapidly upon dilution, i.e., the molecules head for open places at the surface of the water with the resulting precipitation of the therapeutic agent. Fortunately, this short-coming can be avoided by using lipids with a long fatty acid chain or two fatty acid chains, specifically phospholipids and sphingolipids, or polymers, specifically block copolymers to form the micelles.

Polymeric micelles have been prepared that exhibit CMOs as low as $10^{-6}$ M (molar). Thus, they tend to be very stable while at the same time showing the same beneficial characteristics as surfactant micelles. Any micelle-forming polymer presently known in the art or as such may become known in the future may be used in the method of this invention. Examples of micelle-forming polymers are, without limitation, methoxy poly(ethylene glycol)-b-poly($\epsilon$-caprolactone), conjugates of poly(ethylene glycol) with phosphatidyl-ethanolamine, poly(ethylene glycol)-b-polyesters, poly(ethylene glycol)-b-poly(L-aminoacids), poly(N-vinylpyrrolidone)-bl-poly(orthoesters), poly(N-vinylpyrrolidone)-b-polyanhydrides and poly(N-vinylpyrrolidone)-b-poly(alkyl acrylates).

In addition to the classical spherical micelles described above, the methods of this invention may use constructs known as synthetic worm micelles. Worm micelles, as the name suggests, are cylindrical in shape rather than spherical. They are prepared by varying the weight fraction of the hydrophilic polymer block to the total block copolymer molecular weight in the hydrophilic polymer-b-hydrophobic polymer structure discussed above for preparing spherical micelles. Worm micelles have the potential advantage of not only being bio-inert and stable as are spherical polymeric micelles but also of being flexible. Polyethylene oxide has been used extensively to create worm micelles with a number of hydrophobic polymers such as, without limitation, poly (lactic acid), poly($\epsilon$-caprolactone), poly(ethylethylene) and polybutadiene. A representative description of worm micelle formation, characterization and drug loading can be found in Kim, Y., et al., *Nanotechnology,* 2005, 16:S484-S491. The techniques described there as well as any other that is currently known or may become known in the future may be used in method of this invention.

As used herein, a "liposome" refers to a core-shell structure in which the shell comprises phospholipids or sphigolipids that surround a usually liquid, and in most cases aqueous, core.

Phospholipids are molecules that have two primary regions, a hydrophilic head region comprised of a phosphate of an organic molecule and one or more hydrophobic fatty acid tails. In particular, naturally-occurring phospholipids have a hydrophilic region comprised of choline, glycerol and a phosphate and two hydrophobic regions comprised of fatty acid. When phospholipids are placed in an aqueous environment, the hydrophilic heads come together in a linear configuration with their hydrophobic tails aligned essentially parallel to one another. A second line of molecules then aligns tail-to-tail with the first line as the hydrophobic tails attempt to avoid the aqueous environment. To achieve maximum avoidance of contact with the aqueous environment, i.e., at the edges of the bilayers, while at the same time minimizing the surface area to volume ratio and thereby achieve a minimal energy conformation, the two lines of phospholipids, know as a phospholipid bilayer or a lamella, converge into a sphere and in doing so entrap some of the aqueous medium, and whatever may be dissolved or suspended in it, in the core of the sphere. Examples of phospholipids that may be used to create liposomes are, without limitation, 1,2-dimyristroyl-sn-glycero-3-phosphocholine, 1,2-dilauroyl-sn-glycero-3-phosphocholine, 1,2-distearoyl-sn-glycero-3-phosphocholine, 1,2-dimyristoyl-sn-glycero-3-phosphoethanolamine, 1,2-dipalmitoyl-sn-glycero-3-phosphoethanolamine, 1,2-dioleoyl-sn-glycero-3-phosphate monosodium salt, 1,2-dipalmitoyl-sn-glycero-3-[phosphor-rac-(1-glycerol)]sodium salt, 1,2-dimyristoyl-sn-glycero-3-[phospho-L-serine]sodium salt, 1,2-dioleoyl-sn-glycero-3-phosphoethanolamine-N-glutaryl sodium salt and 1,1',2,2'-tetramyristoyl cardiolipin ammonium salt.

While liposomes are generally relatively unstable in the presence of blood serum components, in particular serum proteins such as low density lipoproteins (LDLs), high density lipoproteins (HDLs) and human serum albumin (HAS), for the purposes of this invention liposomes formed of especially susceptible phospholipids are presently preferred and even more preferred at present are combinations of these phospholipids that create irregular structure in the phospholipid bilayer that forms the shell of the liposome. Such phospholipids include, without limitation, soy phosphatidylglycerol, hydrogenated soy phosphatidylglycerol, distearoyl phosphatidylglycerol, soy phosphatidylcholine and hydrogenated soy phosphatidylcholine and, as noted above, combinations thereof.

Liposomes may be unilamellar, composed of a single bilayer, or they may be multilamellar, composed of two or more concentric bilayers. Liposomes range from about 20-100 nm diameter for small unilamellar vesicles (SUVs), about 100-5000 nm for large multilamellar vesicles and ultimately to about 100 microns for giant multilamellar vesicles (GMVs). LMVs form spontaneously upon hydration with agitation of dry lipid films/cakes which are generally formed by dissolving a lipid in an organic solvent, coating a vessel wall with the solution and evaporating the solvent. Energy is then applied to convert the LMVs to SUVs, LUVs, etc. The energy can be in the form of, without limitation, sonication, high pressure, elevated temperatures and extrusion to provide smaller single and multi-lamellar vesicles. During this process some of the aqueous medium is entrapped in the vesicle. Generally, however, the fraction of total solute and therefore the amount of therapeutic agent entrapped tends to be rather low, typically in the range of a few percent. Recently, however, liposome preparation by emulsion templating (Pautot, et al., *Langmuir*, 2003, 19:2870) has been shown to result in the entrapment of virtually 100% of aqueous solute. Emulsion templating comprises, in brief, the preparation of a water-in-oil emulsion stabilized by a lipid, layering of the emulsion onto an aqueous phase, centrifugation of the water/oil droplets into the water phase and removal of the oil phase to give a dispersion of unilamellar liposomes. This method can be used to make asymmetric liposomes in which the inner and outer monolayers of the single bilayer contain different lipids.

The diblock copolymers discussed above with regard to micelle formation can be further modified to form bilayer structures similar to liposomes. The structures are referred to as polymersomes. Depending on the length and chemical nature of the polymers in the diblock copolymer, polymersomes can be substantially more robust that liposomes. In addition, the ability to control completely the chemical nature of each block of the diblock copolymer permits tuning of the polymersome's composition to fit the desired application. For example, membrane thickness can be controlled by varying the degree of polymerization of the individual blocks. Adjusting the glass transition temperatures of the blocks will affect the fluidity and therefore the permeability of the membrane. Even the mechanism of release can be modified by altering the nature of the polymers.

Polymersomes can be prepared in the same manner as liposomes. That is, a film of the diblock copolymer can be formed by dissolving the copolymer in an organic solvent, applying a film of the copolymer-containing solvent to a vessel surface, removing the solvent to leave a film of the copolymer and then hydrating the film. This procedure, however, tends to result is a polydispersion of micelles, worm micelles and vesicles of varying sizes. Polymersomes can also be prepared by dissolving the diblock copolymer in a solvent and then adding a poor solvent for one of the blocks, which will result in the spontaneous formation of polymersomes.

As with liposomes, polymersomes can be used to encapsulate bioactive agents by including the bioactive agent in the water used to rehydrate the copolymer film. Polymersomes can also be force-loaded by osmotically driving the therapeutic agent into the core of the vesicle. Similarly to liposomes, the loading efficiency of polymersomes is generally low. Recently, however, a technique has been reported that provides polymersomes of relative monodispersivity and high loading efficiency; generation of polymerisomes from double emulsions. Lorenceau, et al., *Langmuir*, 2005, 21:9183-86. The technique involves the use of microfluidic technology to generate double emulsions consisting of water droplets surrounded by a layer of organic solvent. These droplet-in-a-drop structures are then dispersed in a continuous water phase. The diblock copolymer is dissolved in the organic solvent and self-assembles into proto-polymersomes on the concentric interfaces of the double emulsion. The actual polymersomes are formed by completely evaporating the organic solvent from the shell. By this procedure the size of the polymersomes can be finely controlled and, in addition, the ability to maintain complete separation of the internal fluids from the external fluid throughout the process allows extremely efficient encapsulation. This technique, along with any other technique known in the art or as may become known in the future, can be used to prepare carrier vesicles of this invention.

Pharmaceutical compositions of this invention will include a compound herein in an amount effective to achieve the intended purpose. If the pharmaceutical composition is being administered as a pharmaceutical drug, a therapeutically effective amount of a compound or pharmaceutically acceptable composition disclosed herein will depend on the route of administration, the subject, such as without limitation, a human, being treated, and the physical characteristics of the subject. A pharmaceutical composition of this invention comprises a pharmaceutical drug if the administration of the composition is under the supervision of an attending physician or other profession practitioner. The dose can be tailored to achieve a desired effect, but will depend on such factors as weight, diet, concurrent medication and other factors which those skilled in the medical arts will recognize. Determination of a therapeutically effective amount is well within the capability of those skilled in the art, especially in light of the detailed disclosure provided herein. At present, doses of the compounds of this invention for use as pharmaceutical drugs may vary from about 1 mg/day to about 5000 mg/day, preferably at present, about 100 to about 2500 mg/day. The dosage may constitute a single does or a series of two or more doses administered over the course of a day.

It should be noted that the attending physician would know how to and when to terminate, interrupt, or adjust administration due to toxicity or organ dysfunctions. Conversely, the attending physician would also know to adjust treatment to higher levels if the clinical response were not adequate. The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual subject. A program comparable to that discussed above may be used in veterinary medicine.

The compounds of this invention may also constitute dietary supplements rather than pharmaceutical drugs. In such case the dosage will be in the hands of the user although recommendations may be provided. In general, the daily dose may range over the same range as that provided above with regard use of the pharmaceutical composition of this invention as a pharmaceutical drug. Care should be taken and a medical arts practitioner consulted if doses at the high end of the range are desired. A practical guideline for dietary supplement dosing may be the presently acknowledged does for alpha lipoic acid. That is, alpha lipoic acid is available in single dose formats of about 50 mg to 800 mg. It is expected that the compounds of the instant invention may be usable as dietary supplements at about the same single dosage levels. The suggested number of doses per day may vary, which would of course, make the daily dosage multiples of the single dose amount.

Examples

Nine test compounds were synthesized and characterized. The effects of R, S and RS forms of LA, LAM and LAP on multiple signaling pathways were studied in HepG2 cells at 0.2 mM for 8 hours (5.5 mM glucose) using a dual-luciferase reporter array. The reporter is a mixture of Firefly Luciferase gene construct under control of an inducible transcription factor-responsive promoter and an internal control plasmid constitutively expressing Renilla luciferase gene. Each inducible construct monitors changes in the activity of a select transcription factor serving as a marker for activation or suppression of a specific signaling pathway.

This above studies identified previously unknown enantioselective and non-enantioselective pathways differentially affected by LA and amide derivatives. In some cases the racemic compounds activate pathways not activated by either enantiomer. These results provide evidence the racemic compounds should not be considered to be equal mixtures of the R & S-enantiomers, quantitatively or qualitatively and supports the contention that the three forms of each group should be considered pharmacologically distinct. This study also reveals some features common to all compounds or select groupings by enantiomer. The heavy metal response pathway was similarly affected by all nine compounds, which lowered values below control levels. Eight of nine compounds increased peroxisome proliferator-activated receptor (PPAR) activity while SLA alone lowered it. The greatest increase in activity of a pathway by all compounds was activation of the Antioxidant Response Element (ARE) but the magnitude varied widely by compound. RLAM produces the strongest ARE response, 12.5 times greater than RLA but is not clearly enantioselective as RS-LAM produces ~½ the response. SLAM and SLAP similarly induced the xenobiotic response element (XRE) but only SLAM activated the androgen receptor (AR), ARE, heat shock factor (HSF) and the XRE indicating SLAM and SLAP are potential bi-functional inducers activating different subsets of response elements of Phase I-III enzymes. In the LA group, RLA selectively activates retinoic acid response element (RAR) and C/EBP, whereas RS-LA activated the retinoid X receptor (RXR). Activation of FOXO transcription factors is repressed by AKT phosphorylation and thus functions as an inverse marker for PI3K/AKT activity, such that low pathway activity increases the magnitude of the FOXO reporter. The effects of RLA and SLA can be separated as RLA strongly activates PI3K/AKT (shown by the small magnitude of FOXO response) and SLA and RS-LA display minimal and low effect. RS-LA alone in the LA group strongly activates p53, the "DNA-damage" reporter, early growth response 1 (EGR1) and the estrogen receptor (ER). All LAMs increase activating transcription factor 6 (ATF6), glucocorticoid receptor (GR) and AR, whereas only RLAP, amongst the LA and LAP groups, increase AR reporter activity. RLAM selectively activates the progesterone receptor (PR). SLAM selectively activates ER.

Thus, this study identified novel and unanticipated pathways, uniquely or differentially affected by the enantiomers and racemates of each group and provides heretofore unknown information to help further define the structure-activity relationships and mechanisms of action of LA and derivatives.

REFERENCES

1. Shen W, Carlson D A, Packer L, Cadenas E, Liu J. Therapeutic potential of lipoamide and enhanced mitochondrial biogenesis for treatment of insulin resistance. Chapter 5 in Mitochondrial Signaling in Health and Disease (93-111) Eds. Orrenius S, Cadenas E and Packer L. CRC Press, Taylor & Francis Group, Boca Raton, London, New York (2012)
2. Sen C K, Tirosh O, Roy S, Kobayashi M S, Packer L. A positively charged alpha-lipoic acid analogue with increased cellular uptake and more potent immunomodulatory activity. Biochem Biophys Res Commun. 1998 Jun. 18; 247(2):223-8.
3. Tirosh O, Sen C K, Roy S, Kobayashi M S, Packer L. Neuroprotective effects of alpha-lipoic acid and its positively charged amide analogue. Free Radic Biol Med. 1999 June; 26(11-12):1418-26.
4. Guo Q, Tirosh O, Packer L. Inhibitory effect of alpha-lipoic acid and its positively charged amide analogue on nitric oxide production in RAW 264.7 macrophages. Biochem Pharmacol. 2001 Mar. 1; 61(5):547-54.
5. Persson H L, Svensson A I, Brunk U T. Alpha-lipoic acid and alpha-lipoamide prevent oxidant-induced lysosomal rupture and apoptosis. Redox Rep. 2001; 6(5):327-34.
6. Tirosh O. Shilo S, Aronis A, Sen C K. Redox regulation of mitochondrial permeability transition: Effects of uncoupler, lipoic acid and its positively charged analog LA-plus and selenium. BioFactors. Volume 17, Issue 1-4, pages 297-306, 2003.

What is claimed is:

1. A method of treating a disease or disorder, comprising administering a therapeutically effective amount of a pharmaceutical composition comprising a substantially enantiomerically pure R-(+)-lipoamide, a substantially enantiomerically pure S-(−)-lipoamide, an N-substituted substantially enantiomerically pure R-(+)-lipoamide, an N-substituted substantially enantiomerically pure S-(−)-lipoamide or a pharmaceutically acceptable salt of any of the foregoing to a subject in need thereof.

2. The method of claim 1, wherein the pharmaceutical composition modulates a signaling pathway selected from the group consisting of an amino acid deprivation, androgen, antioxidant response, ATF6, C/EBP, cAMP, PKA, cell cycle, DNA damage, EGR1, ER stress, estrogen, GATA, glucocorticoid, heat shock, heavy metal stress, hedgehog, HNF4, hypoxia, interferon regulatory factor, interferon type 1, interferon gamma, KLF4, liver receptor X, MAPK/ERK, MAPK/JNK, MEF2, Myc, Nanog, Notch, NFkB, Oct4, Pax6, PI3K/AKT, PKC/$Ca^{2+}$, PPAR, progesterone, retinoic acid, retinoid X, SOX2, SP1, STATA3, TGFβ, vitamin D, Wnt, and a xenobiotic pathway.

3. The method of claim 1, wherein the condition is selected from the group consisting of diabetes, diabetic neuropathy, glaucoma, cancer, kidney disease, age-related memory loss, Alzheimer's disease, atherosclerosis, bone loss, vascular disease, mitochondrial myopathy, multiple sclerosis, muscular dystrophy, cerebrovascular disease, cognitive impairment, Down's syndrome, endothelial dysfunction, Hepatitis C, inflammation, high blood pressure, high cholesterol, neurodegenerative disease, obesity, Parkinson's disease, retinal leukostasis, retinal ischemia, retinal reperfusion, retinopathy, sepsis, sickle cell anemia, Wilson's disease, age-related loss of liver detoxification, age-related loss of liver regeneration, hepatic cancer, autoimmune disease, degenerative brain disorder, cerebral ischemia, AIDS and a hepatic disorder.

4. The method of claim 3, wherein the condition is selected from the group consisting of age-related loss of liver detoxification, age-related loss of liver regeneration and hepatic cancer.

* * * * *